United States Patent
Slate et al.

(10) Patent No.: US 6,645,169 B1
(45) Date of Patent: Nov. 11, 2003

(54) AIR-IN-TIP JET INJECTOR

(75) Inventors: John B. Slate, San Diego, CA (US); Michael W. Burk, San Marcos, CA (US); Lanny A. Gorton, San Diego, CA (US)

(73) Assignee: Avant Drug Delivery Systems, Inc., San Diego, CA (US)

( * ) Notice: Subject to any disclaimer, the term of this patent is extended or adjusted under 35 U.S.C. 154(b) by 15 days.

(21) Appl. No.: 09/665,849

(22) Filed: Sep. 20, 2000

Related U.S. Application Data

(63) Continuation-in-part of application No. 09/590,857, filed on Jun. 8, 2000, now Pat. No. 6,406,456.

(51) Int. Cl.[7] .......................... A61M 5/30; A61M 37/00
(52) U.S. Cl. ..................... 604/68; 604/70; 604/140
(58) Field of Search ......................... 604/68, 70, 69, 604/71, 93.01, 115, 140, 181, 187, 218; 222/4, 195, 394, 399

(56) References Cited

U.S. PATENT DOCUMENTS

| | | |
|---|---|---|
| 3,640,277 A | 2/1972 | Adelberg |
| 4,059,107 A | 11/1977 | Iriguchi |
| 4,403,609 A | 9/1983 | Cohen |
| 4,680,027 A | 7/1987 | Parsons |
| 4,874,367 A | 10/1989 | Edwards |
| 5,024,656 A | 6/1991 | Gasaway |
| 5,074,843 A | 12/1991 | Dalto |
| 5,190,523 A | 3/1993 | Lindmayer |
| 5,439,643 A * | 8/1995 | Liebert .................. 422/25 |
| 5,503,628 A | 4/1996 | Fetters |
| 5,505,697 A | 4/1996 | McKinnon |
| 5,554,127 A * | 9/1996 | Crouther et al. .......... 206/366 |
| 5,993,412 A * | 11/1999 | Deily et al. ............. 604/140 |

* cited by examiner

Primary Examiner—Brian L. Casler
Assistant Examiner—Catherine Serke
(74) Attorney, Agent, or Firm—Nydegger & Associates

(57) ABSTRACT

A method for injecting a fluid medicament into a patient uses a syringe having a plunger that can be advanced into the syringe chamber. As the plunger is advanced, the medicament is expelled from the chamber through an injection tube that extends from the chamber. Preferably, the injection tube is formed as a cone-shaped funnel with a taper of generally decreasing radius in a distal direction. The steps for the method include creating a gas pocket in the distal portion of the injection tube. Then, as the plunger is advanced into the chamber to accelerate the fluid medicament through the injection tube, the gas pocket allows the accelerating fluid medicament to gain momentum. The change in this momentum as the fluid medicament collides with the skin will generate an impulse force that is manifested as an initial pressure spike. This pressure spike creates a hole in the skin of the patient as the fluid medicament exits the tube. Further advancement of the plunger into the chamber maintains a substantially constant infusion pressure for injecting the fluid medicament through the hole and into the patient.

16 Claims, 1 Drawing Sheet

AIR-IN-TIP JET INJECTOR

This application is a continuation-in-part of application Ser. No. 09/590,857 filed Jun. 8, 2000, now U.S. Pat. No. 6,406,456, which is currently pending. The contents of application Ser. No. 09/590,857 are incorporated herein by reference.

FIELD OF THE INVENTION

The present invention pertains generally to methods for injecting a fluid medicament into a patient. More particularly, the present invention pertains to methods for using needleless (jet) injectors for delivering a fluid medicament to a patient. The present invention is particularly, but not exclusively, useful as a method for generating injection pressures with the fluid medicament that will effectively create a hole in the skin of the patient and subsequently maintain a substantially constant infusion pressure.

BACKGROUND OF THE INVENTION

Needleless injectors have been used for many years for the purpose of infusing fluid medicaments into a patient. Indeed, they have several advantages over needle-type injectors. For instance, needleless injectors lend themselves to schedules where a large number of patients are to be inoculated at the same time. Most importantly, they do not incorporate sharp or pointed projections that can inadvertently stick into the care giver, or into some other third person. In recent years, the avoidance of so-called "sharps," that can cause inadvertent sticks, has been a design objective of many medical devices.

In their operation, all needleless (jet) injectors rely on the generation of fluid pressures in the fluid medicament. Specifically, the purpose of generating these pressures is two-fold. First, it is necessary to create a hole in the skin of the patient. Second, it is necessary to thereafter maintain a substantially constant pressure for infusion of the fluid medicament into the patient through the hole. The magnitude and duration of these fluid pressures will, in large part, depend on the type of injection to be given.

There are basically three different types of injections that may need to be performed by a needleless injector. These are: 1) shallow, intra-dermal injections where the fluid medicament is infused directly into the skin; 2) medium depth, subcutaneous injections where the fluid medicament is infused into the fatty tissue beneath the skin; and 3) deeper intra-muscular injections where the fluid medicament is delivered directly into muscle tissue. Thus, depending on the type of injection that is desired, and the general nature or condition of the patient's skin, the fluid pressure that is necessary to make an appropriate hole can vary from injection to injection.

The mechanics of making an appropriate hole into or through the skin of a patient can be considered in terms of the forces that are generated for this purpose. An important aspect of this consideration involves the impulse-momentum relationships that are created to make an appropriate hole in the skin of a patient. By definition, an impulse force is one that is generated when two bodies collide with each other. In such a collision there is a large reactive force between the bodies that continues over the period of impact. This force (i.e. impulse) can be measured only by its time integral, and is equal to the change of momentum produced in either body. Further, momentum is a dynamic quantity that is conserved within a closed system and which is equal to "mv" where "m" is the mass of the body, and "v" is its velocity. Stated differently, an impulse force can be thought of as being equal to a change in momentum that is equal to the mass of a body times its change in velocity.

Insofar as needleless injectors are concerned, the initial immediate rise of pressure in the fluid medicament that is necessary to create a hole in the skin of a patient is typically generated by driving a drive bar against a syringe plunger. The resultant impulse force then contributes to a pressure rise in the fluid medicament. This, in turn, causes the fluid medicament to penetrate the skin, and thereby create the necessary hole for subsequent infusion. Larger and faster drive bars, of course, would increase the fluid pressure. An example of such a device is provided in U.S. Pat. No. 5,911,703 for an invention of Slate et al. that is entitled "Two-Stage Fluid Medicament Jet Injector" and that is assigned to the same assignee as the present invention.

Heretofore, when using needleless injectors, the practice has been to position a pre-filled injection tube directly against the skin of the patient. This, however, also places the fluid medicament that is in the tube in direct contact with the skin. Consequently, because the fluid medicament is already in contact with the skin, the impulse force that is created as the drive bar impacts the fluid medicament is significantly attenuated by the time its effect is felt between the fluid medicament and the skin of the patient. An initial consequence of this is that the fluid medicament has insufficient momentum to penetrate the skin. Thus, it happens, at least initially, that the fluid medicament can seep around the injector and puddle on the surface of the skin. It would be desirable, however, to effectively generate increased fluid pressures (fluid momentum) for the purpose of creating a hole in the skin of a patient. Preferably, this can be done without necessarily resorting to larger and faster drive bars, while also avoiding the seepage and puddling of the fluid medicament on the skin of the patient.

With needleless injectors there is always the requirement that a jet pressure be developed which is sufficient to cause the fluid medicament to penetrate the skin. One way to accomplish this is to use a heavy drive bar that will generate the necessary momentum. Heavy drive bars, however, also generate an undesirable recoil and, for spring-loaded injector mechanisms, a heavy drive bar will require a spring with a relatively large spring constant. Consequently, depending on the type of mechanism that is used to propel the drive bar, injector mechanisms that use large springs to propel heavy drive bars can be hard to cock. Although lighter drive bars will overcome these less desirable consequences, lighter drive bars will necessarily have less momentum under the same circumstances.

In light of the above, it is an object of the present invention to provide a method for injecting a fluid medicament into a patient that uses a gas pocket in the injection tube of a needleless injector to increase the impulse force of a fluid medicament as it is ejected from the injector for the purpose of creating a hole in the skin of a patient. It is another object of the present invention to provide a method for using a needleless injector to inject a fluid medicament into a patient that is predictable, reliable, controllable, and repeatable. Still another object of the present invention is to provide a method for injecting a fluid medicament into a patient that allows for the generation of greater fluid pressures, while using smaller injection mechanisms. Another object of the present invention is to provide a method for injecting a fluid medicament into a patient that avoids the leakage or seepage of fluid medicament onto the skin of a patient. Still another object of the present invention is to provide a method for injecting a fluid medicament into a patient that minimizes recoil and allows the injector mechanism to be easily cocked. Yet another object of the present invention is to provide a method for injecting a fluid medicament into a patient that is easy to practice, simple to employ and is very cost effective to implement.

SUMMARY OF THE PREFERRED EMBODIMENTS

In accordance with the present invention, a method for injecting a fluid medicament into a patient uses a typical syringe mechanism. Specifically, the syringe will have a fluid chamber and a plunger that can be advanced into, and withdrawn from, the syringe chamber. In its normal operation, as the plunger is advanced into the chamber of the syringe, the fluid medicament will be expelled from the chamber and through an injection tube. As envisioned for the present invention, this injection tube will extend from the chamber and terminate at a distal port. Preferably, between the fluid chamber of the syringe and the distal port, the injection tube is formed as a generally cone-shaped funnel. Specifically, the funnel of the injection tube will have a taper that is of a generally decreasing radius in the distal direction.

The steps for the method of the present invention include initially filling the syringe chamber with a fluid medicament. Then, importantly, a gas pocket is created in the distal portion of the injection tube that is contiguous to the port. Depending of the type of injection to be made (i.e. intra-dermal, subcutaneous, or intra-muscular), and the patient's skin type, the volume of this gas pocket can be varied. In general, the volume of the gas pocket will be in the range of from about one to about twenty microliters. Once the gas pocket has been created, the port of the injection tube can then be positioned against the skin of the patient.

With the port of the injection tube positioned against the skin of the patient, the needleless injector is activated to force the fluid medicament through the port to inject the fluid medicament into the patient. This action can actually be considered as a two-step process. In the first step, the fluid medicament is accelerated through the gas pocket that was initially established in the distal portion of the injection tube. During its accelerated transit of the fluid medicament through the empty distal portion of the injection tube, the fluid medicament gains momentum. Then, on its impact with the skin, an impulse force is generated between the fluid medicament and the skin that is manifested as an initial pressure spike. It is this initial pressure spike that creates the hole in the skin of the patient. Thereafter, in the second step, a substantially constant infusion pressure is maintained for injecting the fluid medicament through the hole into the patient. It happens that the pressure for initially creating the hole will be greater than the subsequent infusion pressure.

Some additional considerations for the present invention are that the initial jet pressure, which creates the hole in the skin of the patient, is generally in a range between about twenty percent (20%) and about five hundred percent (500%) above the initial jet pressures generated when no gas pocket is present in the injection tube. Further, it is to be appreciated that the gas pocket in the injection tube can be created merely by withdrawing the plunger from the chamber. Other methods, of course, can be used to create the gas pocket. For instance, air can be forced into the tip, or fluid can be forced from the tip by shaking or wicking. As envisioned for the methods of the present invention, the gas pocket will preferably have a fluid volume that is in a range between one and about twenty microliters (1–20 $\mu$l).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
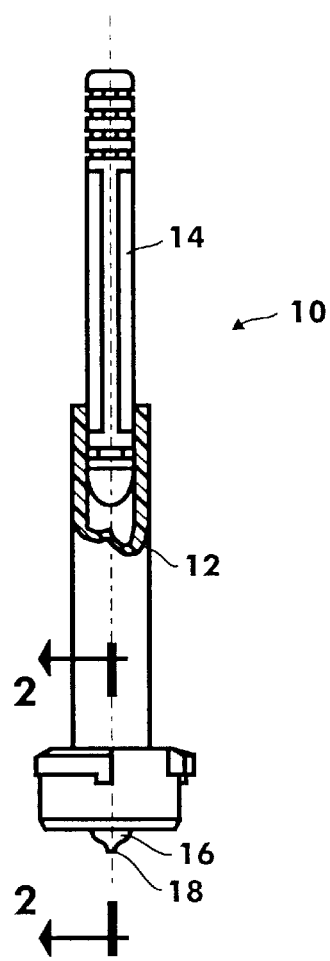
FIG. 1 is an elevational view of a syringe that is useful for.practicing the methods of the present invention, with portions broken away for clarity.

Referring initially to FIG. 1, an injector/syringe that is useable for the methods of the present invention is shown and is generally designated 10. To begin, it is to be appreciated that, although the disclosure for the present invention is given in the context of the injector/syringe 10, the injector/syringe 10 is only exemplary. Indeed, as envisioned by the present invention, any device or apparatus that has the same, similar or equivalent functional attributes as the injector/syringe 10 will suffice.

As shown in FIG. 1, the injector/syringe 10 includes a fluid chamber 12 and a plunger 14 that can be advanced into the chamber 12 or, alternatively, withdrawn from the chamber 12. Also, the injector/syringe 10 is shown to have a tip 16 that is formed with a port 18. A more detailed appreciation of the tip 16 of the injector/syringe 10 is possible with reference to FIG. 2.

Figure 2:
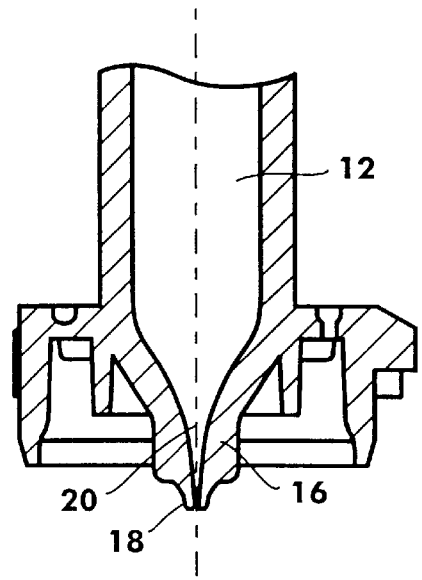
FIG. 2 is a cross sectional view of the injection portion of the syringe as seen along the line 2—2 in FIG. 1.

In FIG. 2 it will be seen that the tip 16 of the injector/syringe 10 is formed with an injection tube 20 that extends from the chamber 12. Importantly, the injection tube 20 establishes fluid communication between the chamber 12 and the port 18. Further, and also importantly, the injection tube 20 is formed with a taper of diminishing cross section in a distal direction. Stated differently, the injection tube 20 decreases in diameter in the distal direction (the distal direction is from the chamber 12 toward the port 18). The exact configuration of the injection tube 20 for the injector/syringe 10 is somewhat a matter of design choice. It is, however, preferable that the surface transition in the injection tube 20 between the chamber 12 and the port 18 be smooth, and have a minimum of irregularities, such as so-called "shoulders."

Figure 3:
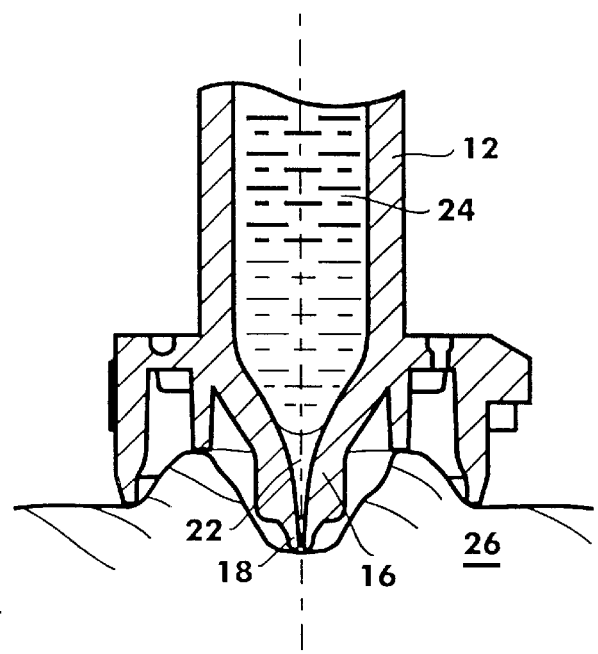
FIG. 3 is a view of the injection portion of the syringe as shown in FIG. 2 with a gas pocket created in the injection portion.

To prepare the injector/syringe 10 for an injection, it is shown in FIG. 3 that it is necessary to first create a gas pocket 22 in the tip 16. This can be accomplished in any of several ways. For one, after the chamber 12 has been filled with a fluid medicament 24, the plunger 14 can be withdrawn a predetermined distance. For another, a pre-filled injector/syringe 10 can be mechanically engaged with an injecting device (not shown) which will automatically withdraw the plunger 14 through the predetermined distance. Still other ways for creating the gas pocket 22, all well known in the pertinent art, can be used for the purposes of the present invention. In all cases, the gas pocket 22 will be created in the injection tube 20 between the chamber 12 and the port 18 of tip 16. Preferably, the gas pocket 22 is contiguous with the port 18.

Depending on the type of injection that is to be given, and the condition and nature of the patient's skin where the injection is to be made, the size of the gas pocket 22 can be varied. For example, for an intra-dermal injection where the depth of penetration is minimal, the gas pocket 22 will preferably be small. As the depth of penetration for the fluid medicament 24 is increased (e.g. subcutaneous and intramuscular injections), the size of the gas pocket 22 will be proportionately increased. Also, when considering skin condition, it will be appreciated that as a patient's skin is thicker and tougher it may be desirable or necessary to increase the size of the gas pocket 22. For most applications, the size or volume of the gas pocket 22 will be in a range between one and twenty microliters (1–20 $\mu l$).

In operation, after a gas pocket 22 has been created in the tip 16 of the injector/syringe 10, the port 18 of the tip 16 is positioned against the skin 26 of a patient. The plunger 14 is then rapidly advanced into the fluid chamber 12 by means well known in the art. As the plunger 14 is advanced into the chamber 12, the fluid medicament 24 is urged from the chamber 12 and through the injection tube 20. Due to the gas pocket 22, however, there is little, if any, resistance to the movement of the fluid medicament 24 through the injection tube 20. Thus, at least initially, the fluid medicament 24 is accelerated as it passes through the injection tube 20. In doing so, the fluid medicament 24 gains momentum.

Figure 4:
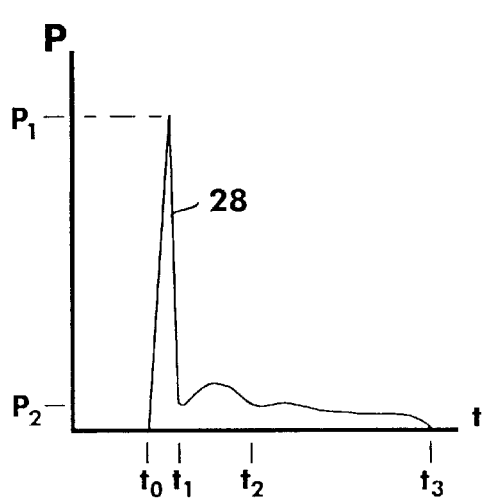
FIG. 4 is a time graph depicting the fluid pressures in the injection portion of the syringe during an injection.

The consequence of the fluid medicament 24 gaining momentum as it passes through the space in the injection tube 20 that is created by the gas pocket 22 will, perhaps, be best appreciated with reference to FIG. 4. When referring to FIG. 4, consider that the injection process is initiated at time $t_0$. Also consider that there can be effectively two different ways in which to begin the infusion process. These depend on the velocity of a drive bar as it initially impacts against the plunger 14. For a high velocity impact, i.e. one that is characterized by a low mass drive bar having a relatively long acceleration distance before hitting the plunger 14, the effect of gas pocket 22 will be more pronounced than for a low velocity impact. In the case of a low velocity impact, the drive bar will typically have a higher mass and shorter acceleration distance. As between these two, the following discussion is focused more on the high velocity impact scenario. The general notions between the two types of impacts, however, are essentially the same.

FIG. 4 shows that at time $t_0$ the pressure, P, of the fluid medicament 24 against the skin 26 is dramatically increased to an extreme pressure $p_1$. In this case, pressure $p_1$ results from the impulse force that is generated when the fluid medicament 24 accelerates through the gas pocket 22 and collides with the skin 26 of the patient. The momentum of the fluid medicament 24 is then dissipated as the pressure, P, changes rapidly from $p_1$ to a much reduced pressure at time $t_1$. Pressure $p_1$ has a value in a range between about twenty percent (20%) to five hundred percent (500%) greater than the peak pressure between $t_1$ to $t_2$. Thereafter the pressure, P, tends to settle at an infusion pressure $p_2$ at the time $t_2$ and it will generally remain at the infusion pressure $p_2$ until the time $t_3$ when the infusion is completed. In this sequence, the pressure spike 28 that is generated as pressure, P, goes from zero, to an extreme pressure $p_1$, and then back toward $p_2$, in a time interval that is in a range from about ten microseconds to about one hundred microseconds (i.e. $\Delta t$ from $t_0$ to $t_1$ is around 10–100 $\mu$sec). On the other hand, the total time for the creation of appropriate hole in the skin 26 of the patient will be in a range from about one half millisecond to about two milliseconds (i.e. $\Delta t$ from to to $t_2$ is around 0.5–2 msec). As is to be understood for the present invention, the extreme pressure $p_1$ between $t_0$ and $t_1$ is directly attributable to the presence of the gas pocket 22. Recall, an appropriate hole takes into consideration the type of injection and the condition of the skin 26.

After a hole has been created in the skin 26 of a patient, a substantially constant pressure, $p_2$, can be maintained for an appropriate time duration (e.g. $t_2$ to $t_3$) to effect an infusion or injection of the fluid medicament 24 to the patient. For purposes of the present invention, the highest pressure during the pressure spike 28 will typically be in a range between twenty percent (20%) and five hundred percent (500%) greater than the peak pressure between time $t_1$ and $t_2$. The time duration of the pressure spike 28 (i.e. $t_0$ to $t_1$) will be approximately 10–100 $\mu$sec, and the infusion pressure, $p_2$, will typically be in a range between less than 300 psi and a value less than about 50% of the extreme pressure $p_1$ ($p_2$=<300 psi; or <0.5 $p_1$). The duration of an infusion (i.e. $t_2$ to $t_3$) will be as desired.

While the particular Air-In-Tip Jet Injector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for injecting a fluid medicament into a patient which comprises the steps of:

holding said fluid medicament in a chamber, said chamber having a port for ejecting said fluid medicament therethrough;

creating a pocket of gas in said chamber, said pocket of gas being located in said chamber contiguous to said port;

positioning said port against the patient; and thereafter forcing said gas and said fluid medicament through said port for injection of said fluid medicament into the patient.

2. A method as recited in claim 1 further comprising the step of forming said chamber with an injection tube extending therefrom to establish fluid communication between said chamber and said port.

3. A method as recited in claim 2 wherein said injection tube is formed as a cone-shaped funnel with a taper of generally decreasing radius in a distal direction through said injection tube from said chamber toward said port.

4. A method as recited in claim 2 further comprising the steps of:

accelerating said fluid medicament through said pocket of gas and said tube, said tube having an empty distal portion for generating an initial pressure spike during transit of said fluid medicament through said distal portion, said pressure spike having a first pressure for creating a hole in the skin of the patient as said fluid medicament exits said tube; and maintaining a substantially constant infusion pressure for injecting said fluid medicament through the hole into the patient, said first pressure being greater than said infusion pressure.

5. A method as recited in claim 1 wherein said chamber is a component of a syringe, wherein said syringe includes a plunger and said plunger is positioned for advancement into said chamber and, alternatively, for withdrawal from said chamber, and wherein said forcing step is accomplished by advancing said plunger into said chamber to expel said fluid medicament therefrom.

6. A method as recited in claim 5 further comprising the step of withdrawing said plunger from said chamber to create said pocket of gas.

7. A method as recited in claim 1 wherein said pocket of gas has a fluid volume in a range between one and twenty microliters (1–20 µl).

8. A method for injecting a fluid medicament into a patient which comprises the steps of:

providing a chamber containing a fluid medicament;

extending an injection tube from said chamber, said injection tube being in fluid communication with said chamber, and said injection tube having a distal portion filled with a pocket of gas with said fluid medicament proximal thereto; and forcing said gas and said fluid medicament from said chamber and through said injection tube to inject said fluid medicament into the patient by accelerating said fluid medicament through said distal portion of said injection tube to generate an initial pressure spike during transit of said fluid medicament through said distal portion, said pressure spike having a first pressure for creating a hole in the skin of the patient as said fluid medicament exits said tube, and maintaining a substantially constant infusion pressure for injecting said fluid medicament through the hole into the patient, said first pressure being greater than said infusion pressure.

9. A method as recited in claim 8 wherein said injection tube is formed as a cone-shaped funnel with a taper of generally decreasing radius in a distal direction through said injection tube from said chamber.

10. A method as recited in claim 8 wherein said chamber is a component of a syringe, wherein said syringe includes a plunger and said plunger is positioned for advancement into said chamber and, alternatively, for withdrawal from said chamber, and wherein said forcing step is accomplished by advancing said plunger into said chamber to expel said fluid medicament therefrom.

11. A method as recited in claim 10 further comprising the step of withdrawing said plunger from said chamber to create said pocket of gas.

12. A method as recited in claim 11 wherein said pocket of gas has a fluid volume in a range between one and twenty microliters (1–20 µl).

13. A method for injecting a fluid medicament into a patient which comprises the steps of:

accelerating a fluid medicament through a tube, said tube having an empty distal portion for generating an initial pressure spike during transit of said fluid medicament through said distal portion, said pressure spike having a first pressure for creating a hole in the skin of the patient as said fluid medicament exits said tube; and maintaining a substantially constant infusion pressure for injecting said fluid medicament through the hole into the patient, said first pressure being greater than said infusion pressure.

14. A method as recited in claim 13 herein said tube is a component of a syringe having a chamber and a plunger, and wherein said plunger is positioned for advancement into said chamber and, alternatively, for withdrawal from said chamber, and wherein said accelerating step and said maintaining step are accomplished by advancing said plunger into said chamber to expel said fluid medicament therefrom.

15. A method as recited in claim 13 wherein said empty distal portion is created by a pocket of gas.

16. A method as recited in claim 15 wherein said pocket of gas has a fluid volume in a range between one and twenty microliters (1–20 µl).

* * * * *